United States Patent [19]

Rolinski et al.

[11] 4,231,248
[45] Nov. 4, 1980

[54] LASER TENSILE TEST SAMPLE HOLDER

[75] Inventors: Edmund J. Rolinski, Dayton, Ohio; Bernard Laub, Cupertino, Calif.

[73] Assignee: The United States of America as represented by the Secretary of the Air Force, Washington, D.C.

[21] Appl. No.: 48,875

[22] Filed: Jun. 15, 1979

[51] Int. Cl.³ .............................................. G01N 3/08
[52] U.S. Cl. ...................................... 73/15.6; 73/147; 73/856
[58] Field of Search ...................... 73/432 R, 15.6, 147

[56] References Cited

U.S. PATENT DOCUMENTS

| 2,917,920 | 12/1959 | Robinette | 73/15.6 |
| 4,114,018 | 9/1978 | Allmen | 73/432 L |

*Primary Examiner*—S. Clement Swisher
*Attorney, Agent, or Firm*—Joseph E. Rusz; Richard J. Killoren

[57] ABSTRACT

A test sample support for flat plate test samples used in the simultaneous laser, wind tunnel and tensile machine testing having a cantilever box frame member supported on the tensile machine with an adjustable sample alignment member and a stationary sample alignment member supported on the box frame member. Test sample backing members are adjustably supported on box frame member adjacent the stationary sample alignment member and on the adjustable sample alignment member. Two sample retainer buttons are secured to the stationary sample alignment member and two sample retainer buttons are secured to the adjustable sample alignment member. The stationary sample support member is positioned upstream of the test sample and has a sharp leading edge to provide a well defined flow field over the test sample.

4 Claims, 4 Drawing Figures

1

LASER TENSILE TEST SAMPLE HOLDER

RIGHTS OF THE GOVERNMENT

The invention described herein may be manufactured and used by or for the Government of the United States for all governmental purposes without the payment of any royalty.

BACKGROUND OF THE INVENTION

This invention relates to a sample holder for use in the simultaneous laser, wind tunnel and tensile machine testing of flat plate test samples. In the simulation of flight encounters with high energy laser radiation, test procedures are required that can provide simulation of the laser intensity, aerodynamic flow fields and mechanical loads. These flight conditions have been simulated with a $CO_2$ laser, a subsonic wind tunnel and a tensile test machine.

In attempts at simultaneous laser, wind tunnel and tensile machine testing, post test examinations of the soot patterns indicate separation and recirculating flow over the test sample. This was determined to result from twisting of the sample during application of the tensile loading of the sample which causes impingement of the wind tunnel flow on the side edge of the sample. The problem would not exist if the tensile machine could be adjusted such that the target plane of the test sample would always be aligned and positioned coplaner with the side wall of the wind tunnel exit nozzle. However, fine adjustment of the tensile machine is very difficult due to the nature of the positioning system.

BRIEF SUMMARY OF THE INVENTION

According to this invention a test sample support is provided which has a stationary test sample alignment plate member and an adjustable test sample alignment plate member secured to a cantilever support member. The cantilever is secured to a support bracket which is secured to the tensile machine frame. Test sample backing members are adjustably supported on the cantilever support member and the adjustable alignment member. Button retainers are secured to the stationary alignment member and the adjustable alignment member for holding the test sample in engagement with the test sample backing members. The stationary test sample alignment member has a sharp leading edge to provide a well defined flow field over the test sample.

IN THE DRAWINGS

DETAILED DESCRIPTION OF THE INVENTION

Figure 1:
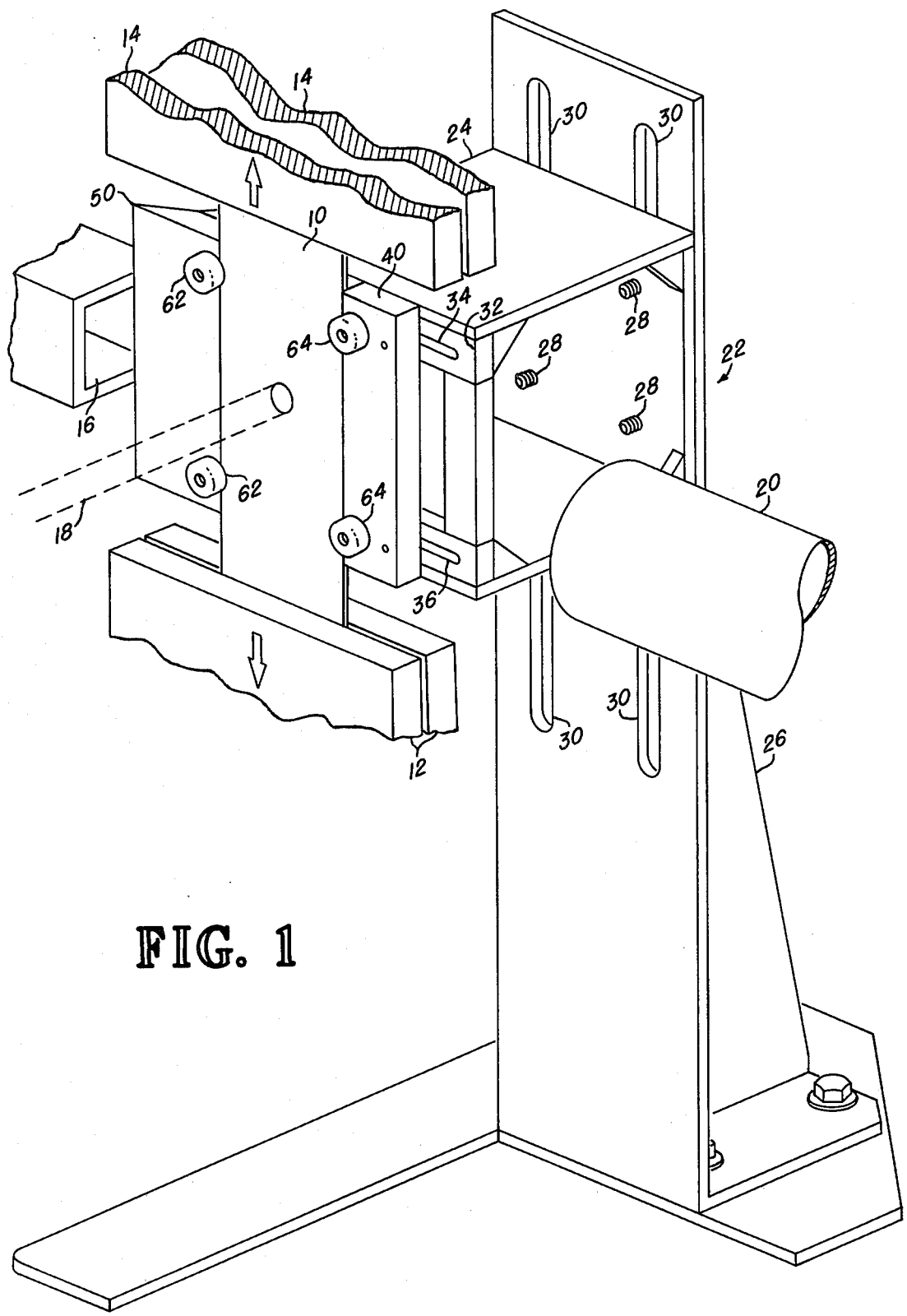
FIG. 1 is a partially schematic view of a laser, wind tunnel, tensile testing system using the sample holder of the invention.

Reference is now made to FIG. 1 of the drawing which shows a flat plate test sample 10 held between tensile machine lower jaws 12 and upper jaws 14, which are positioned to approximately align the test sample parallel to the flow from wind tunnel nozzle 16 which provides a flow substantially perpendicular to the direction of the applied tensile stress. The test sample is irradiated by a laser beam along a beam path perpendicular to the sample as indicated at 18 which may be from a $CO_2$ laser. The wind tunnel exhaust duct is shown at 20.

Figure 2:
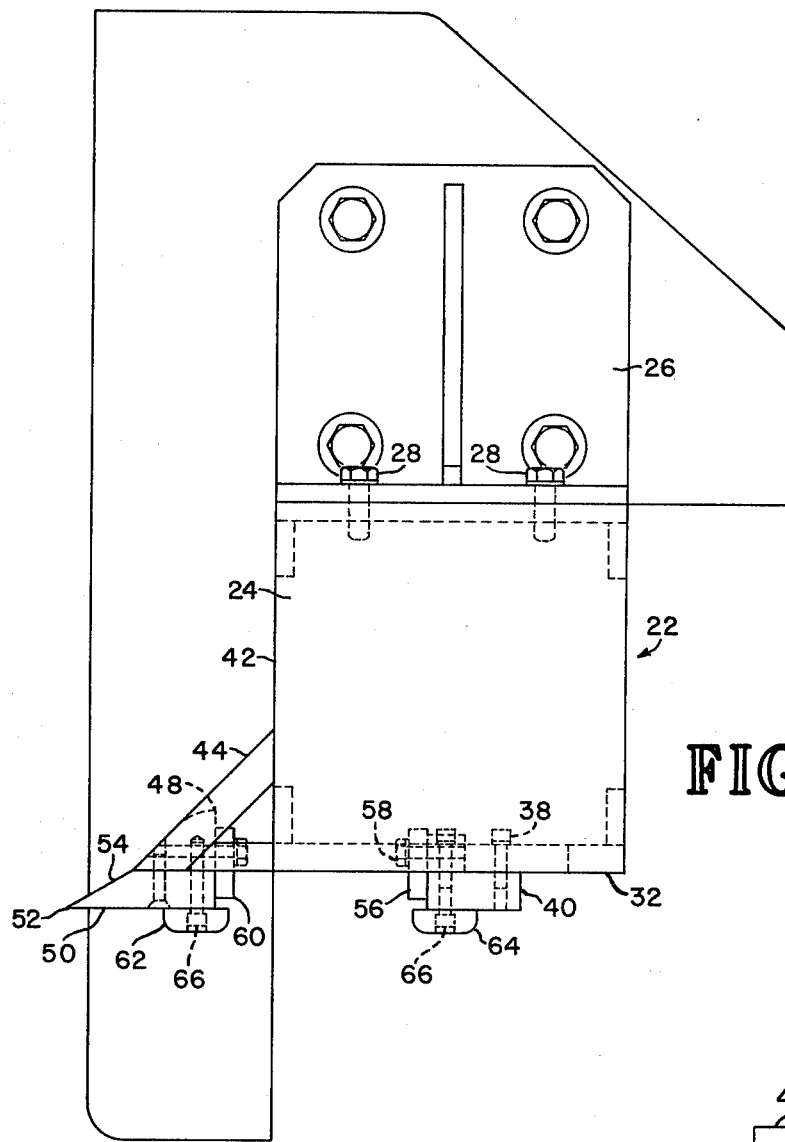
FIG. 2 is a partially schematic top view of the sample holder used in the device of FIG. 1.

To hold the test sample 10 substantially parallel to the wind tunnel flow during the test procedure, a test sample holder 22 is provided. The test sample holder includes a cantilever box frame member 24 adjustably secured to a support bracket 26 by means of bolts 28 which are threaded into the back of box frame member 24 and which are slidable in slots 30. The support bracket 26 is adapted to be secured to the tensile machine frame in a conventional manner, such as with C-clamps, not shown. The box frame member 24 and the support bracket 26 may be assembled by welding the parts together. A front plate member 32 on box 24 has slots 34 and 36 to receive bolts 38, one of which is shown in FIG. 2, to permit adjustment of a movable sample alignment member 40. The plate member 32 extends beyond the edge 42 of the box frame member and is braced by two brackets 44, one of which is shown in FIG. 2. A flow guide and support member 48 is secured to the extended portions of plate member 32 between the two brackets 44. A stationary sample alignment member 50 is secured to the extended portion of plate member 32. The stationary sample alignment member 50 has a sharp leading edge 52 and a surface 54 which forms a continuous surface with the flow guide member 48.

Figure 4:
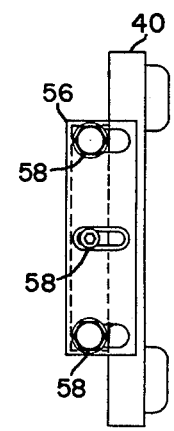
FIG. 4 shows the movable sample alignment member for the sample holder of FIG. 1 with a sample backing member attached.
Figure 3:
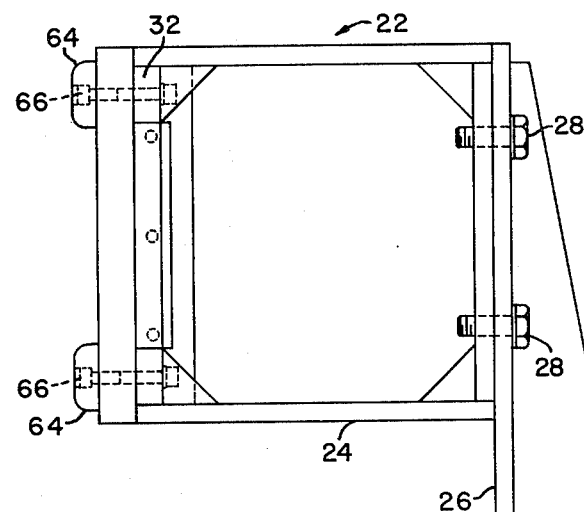
FIG. 3 is a partially schematic side view of the sample holder used in the device of FIG. 1.

An adjustable sample backing member 56 is secured to the movable sample alignment member 40 by means of bolts 58, as shown in FIG. 4. An adjustable sample backing member 60 is secured to the flow guide member 48, adjacent stationary sample alignment member 50, in a similar manner. The backing members 56 and 60 permit adjustment for different sample thicknesses so that the front surface of the sample will be aligned with the front surface of sample alignment members 40 and 50 to provide a smooth flow from the wind tunnel over the sample alignment members and the test sample.

Two sample retainer buttons 62 are secured to the stationary sample alignment member 50 and two sample retainer buttons 64 are secured to the movable sample alignment member 40 with screws 66.

In the operation of the device the sample is first secured in the sample holder by placing the sample between plates 40 and 50 with the center of the sample approximately centered along plates 40 and 50. The sample is then placed against plate 50 and plate 40 is moved into engagement with the other side of the sample. Screws 38 are then tightened to hold the sample. With the use of a straight edge, the laser beam target surface of the sample is made flush with the surface of members 40 and 50 with backing members 56 and 60 being adjusted to position the sample. Screws 66 are then tightened until the buttons 62 and 64 just make contact with the surface of the sample without loading the sample.

The sample holder is then positioned on the lower cross head of the tensile machine, not shown, which has been positioned for the particular sample length used. The sample holder is moved to approximately center the sample in the jaws. The tensile test machine is then moved to approximately align the sample with the flow from nozzle allowing clearance so that the edge 52 does not contact the nozzle 16. The sample is then clamped in the jaws of the tensile test machine.

The screws 38 are then loosened to permit movement of plate 40. Screws 28 are loosened to vertically center the sample holder on the sample. The screws 28 are again tightened to secure the box frame 24 to the bracket 26. Plate 40 is then moved to just make contact with the sample, but not load the sample, and the screws 28 are again tightened.

The sample holder and jaws 12 and 14 are rotated to substantially align the test sample target surface parallel to the air flow from nozzle 16. The tensile machine jaws are then locked to prevent rotation of the jaws. The sample holder bracket 26 is then clamped to the lower cross head of the tensile machine with C-clamps. The sample is then ready for simultaneous laser, wind tunnel and tensile testing.

After each test the samples can be removed and a new sample installed merely by movement of movable sample alignment member 40. If a sample of a different thickness is used adjustment of backing members 56 and 60 will also be required. Other components of the tensile machine and sample holder should not require adjustment once initial alignment is made.

While only four retainer buttons are shown for holding the sample, more may be provided for example if the sample holder were used with a system for applying compression loads.

There is thus provided a sample holder for use in the simultaneous laser, wind tunnel and tensile testing of flat plate test samples.

We claim:

1. In combination with a system for the simultaneous laser, wind tunnel and tensile machine testing of flat plate test samples wherein the tensile machine is located to approximately align the test sample parallel to the flow from a wind tunnel nozzle; a test sample holder for maintaining substantial alignment of the test sample parallel to the wind tunnel flow, comprising: a frame member; a stationary sample alignment member secured to the frame member, upstream in the wind tunnel flow from the test sample; an adjustable sample alignment member secured to the frame member, downstream in the wind tunnel flow from the test sample; means for supporting said frame member on the tensile machine with the stationary alignment member and the adjustable alignment member aligned substantially parallel to the flow from the wind tunnel nozzle; means for positioning the test sample with respect to the stationary alignment member and the adjustable alignment member to provide a smooth flow from the wind tunnel across the stationary alignment member, the test sample and the adjustable alignment member.

2. The device as recited in claim 1 wherein said stationary sample alignment member includes a sharp edge on the side remote from the test sample to thereby provide a sharp edge to the flow from the wind tunnel nozzle.

3. The device as recited in claim 2 wherein said frame member is a cantilever box shaped frame member; said means for supporting said frame member on the tensile machine is a bracket adapted to be secured to the tensile machine; means for adjustably securing the cantilever box shaped frame member on said bracket.

4. The device as recited in claim 3 wherein said means for positioning the test sample with respect to the stationary alignment member and the adjustable alignment member includes a first test sample backing member adjustably secured to said frame member adjacent the stationary sample alignment member; a second test sample backing member adjustably secured to said movable sample alignment member; a plurality of test sample retainer buttons secured to said stationary sample alignment member and a plurality of retainer buttons secured to the adjustable sample alignment member.

* * * * *